(12) United States Patent
Xiong et al.

(10) Patent No.: US 7,504,425 B2
(45) Date of Patent: Mar. 17, 2009

(54) COMPOUNDS USEFUL IN THE TREATMENT OF ANTHRAX AND INHIBITING LETHAL FACTOR

(75) Inventors: Yusheng Xiong, Plainsboro, NJ (US); Kevin Chapman, Scotch Plains, NJ (US); Suresh Singh, Kendall Park, NJ (US); Jian Guo, Scotch Plains, NJ (US); Arthur A. Patchett, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 436 days.

(21) Appl. No.: 10/509,972

(22) PCT Filed: May 23, 2003

(86) PCT No.: PCT/US03/16336

§ 371 (c)(1),
(2), (4) Date: Oct. 1, 2004

(87) PCT Pub. No.: WO03/101382

PCT Pub. Date: Dec. 11, 2003

(65) Prior Publication Data

US 2005/0148629 A1 Jul. 7, 2005

Related U.S. Application Data

(60) Provisional application No. 60/383,996, filed on May 29, 2002.

(51) Int. Cl.
A61K 31/415 (2006.01)
A61K 31/335 (2006.01)
C07D 233/00 (2006.01)
C07D 321/00 (2006.01)

(52) U.S. Cl. .............. 514/385; 514/449; 548/300.1; 549/200

(58) Field of Classification Search .......... 514/385, 514/449; 548/300.1; 549/200
See application file for complete search history.

(56) References Cited

U.S. PATENT DOCUMENTS

| | | | |
|---|---|---|---|
| 4,962,230 A | 10/1990 | Takaya et al. | |
| 5,239,078 A | 8/1993 | Galardy et al. | |
| 5,478,820 A | 12/1995 | Betts et al. | |
| 5,559,267 A | 9/1996 | Burk | |
| 5,591,631 A | 1/1997 | Leppla et al. | |
| 5,677,274 A | 10/1997 | Leppla et al. | |
| 5,712,300 A * | 1/1998 | Jacobsen ............... 514/389 |
| 5,773,438 A | 6/1998 | Levy et al. | |
| 5,804,593 A | 9/1998 | Warpehoski et al. | |
| 5,863,949 A | 1/1999 | Robinson et al. | |
| 5,892,112 A | 4/1999 | Levy et al. | |
| 6,022,893 A | 2/2000 | Sakai et al. | |
| 6,143,744 A | 11/2000 | Broka et al. | |
| 6,150,394 A | 11/2000 | Watanabe et al. | |
| 6,218,389 B1 * | 4/2001 | Almstead et al. ....... 514/237.5 |
| 6,225,311 B1 | 5/2001 | Levin et al. | |
| 6,277,877 B1 | 8/2001 | Hoover et al. | |
| 6,277,987 B1 | 8/2001 | Kukkola et al. | |
| 6,803,379 B2 | 10/2004 | Fernandez-Pol et al. | |
| 6,893,835 B2 | 5/2005 | Duesbery et al. | |
| 6,911,203 B2 | 6/2005 | Duesbery et al. | |
| 6,927,068 B2 | 8/2005 | Simonson et al. | |
| 6,979,449 B1 | 12/2005 | Mock | |
| 2003/0224403 A1 | 12/2003 | Popov et al. | |
| 2004/0006040 A1 | 1/2004 | Schechter | |
| 2004/0076638 A1 | 4/2004 | Siloach et al. | |
| 2004/0138103 A1 | 7/2004 | Patt | |
| 2004/0235136 A1 | 11/2004 | Singh et al. | |
| 2005/0085504 A1 | 4/2005 | Nelson et al. | |
| 2005/0113344 A1 | 5/2005 | Li et al. | |
| 2005/0148629 A1 | 7/2005 | Xiong et al. | |
| 2005/0287074 A1 | 12/2005 | Carpenter et al. | |
| 2006/0084688 A1 | 4/2006 | Barta et al. | |
| 2006/0246532 A1 | 11/2006 | Frucht et al. | |
| 2007/0027064 A1 | 2/2007 | Appelbaum | |
| 2007/0054861 A1 | 3/2007 | Rougeot et al. | |
| 2007/0117848 A1 | 5/2007 | Puerta et al. | |
| 2007/0142318 A1 | 6/2007 | Sonenshein | |
| 2007/0219382 A1 | 9/2007 | Dreher et al. | |

(Continued)

FOREIGN PATENT DOCUMENTS

| | | |
|---|---|---|
| EP | 178911 | 10/1985 |
| EP | 0 757 984 B1 | 8/1996 |
| EP | 0 950 656 B1 | 2/1999 |
| EP | 0 950 656 A1 | 10/1999 |
| EP | 1 069 110 A1 | 1/2001 |
| EP | 1 486 207 A3 | 12/2004 |
| EP | 0 950 656 B1 | 4/2007 |

(Continued)

OTHER PUBLICATIONS

Scozzafava A et al (2000) Carbonic anhydrase and matrix metalloproteinase inhibitors: sulfonylated amino acid hydroxamates with MMP inhibitory properties act as efficient inhibitors of CA isozymes I, II, IV, and N-hydroxysulfonamides inhibit both these zinc enzymes. J Med Chem, vol. 43, pp. 3677-3687.*

(Continued)

*Primary Examiner*—Rei-Tsang Shiao
*Assistant Examiner*—Susannah Chung
(74) *Attorney, Agent, or Firm*—Julie M. Lake; Sheldon O. Heber

(57) ABSTRACT

This invention relates to compounds of formula (I), and a method for treating anthrax or inhibiting lethal factor by administrating a composition containing a compound of formula (I) and a pharmaceutically acceptable carrier. This invention further relates to the use of the compounds of formula (I) to treat other conditions related to an anthrax infection.

8 Claims, No Drawings

FOREIGN PATENT DOCUMENTS

| | | |
|---|---|---|
| JP | 10-204059 A | 8/1998 |
| JP | 11-035557 A | 2/1999 |
| JP | 11-501910 A | 2/1999 |
| JP | 11-246527 A | 9/1999 |
| JP | 2001-503400 A | 3/2001 |
| JP | 2001-513484 A | 8/2001 |
| JP | 2001-513484 A | 9/2001 |
| WO | WO 97/27174 A1 | 1/1997 |
| WO | WO 97/05865 A1 | 2/1997 |
| WO | WO 97/27174 A1 | 7/1997 |
| WO | WO 98/17645 A1 | 4/1998 |
| WO | WO 98/18754 A1 | 5/1998 |
| WO | WO 98/42659 A2 | 10/1998 |
| WO | WO 98/39329 A1 | 11/1998 |
| WO | 99/06340 A2 | 2/1999 |
| WO | WO 99/04780 A1 | 2/1999 |
| WO | WO 99/06340 A2 | 2/1999 |
| WO | WO 99/42443 A1 | 2/1999 |
| WO | WO 99/50439 A2 | 10/1999 |
| WO | WO 99/52889 A1 | 10/1999 |
| WO | WO 99/57097 A2 | 11/1999 |
| WO | WO 99/58947 A2 | 11/1999 |
| WO | WO 00/15213 A1 | 3/2000 |
| WO | WO 01/701690 A1 | 9/2001 |
| WO | WO 2004/011449 A2 | 2/2002 |
| WO | WO 02/072577 A2 | 9/2002 |
| WO | WO 03/035610 A1 | 5/2003 |
| WO | WO 03/051825 A1 | 6/2003 |
| WO | WO 2003/073066 A2 | 9/2003 |
| WO | WO 2003/101382 A2 | 12/2003 |

OTHER PUBLICATIONS

J. M. Clements et al., "Antibacterial Activities and Characterization of Novel Inhibitors of LpxC", 2002, pp. 1793-1799, vol. 46, No. 6, Antimicrobial Agents and Chemotherapy.

D. P. Becker et al., Alpha-Amino-Beta-Sulphone Hydroxamates as Poten MMP-13 Inhibitors that Spare MMP-1:, pp. 2719-2722, vol. 11, Bioorganic Y Medicinal Chemistry Letters.

T. C. Dixon et al., "Anthrax", 1999, pp. 815-820, vol. 341, No. 11, Medical Progress.

M. Mock et al., "Anthrax", 2001, pp. 647-671, vol. 55, Annu. Rev. Microbiol.

G. Vitale et al., "Anthrax Lethal Factor Cleaves the N-Terminus of MAPKKs and Induces Tyrosine/Threonine Phosphorylation of MAPKs in Cultured Macrophages", 1998, pp. 706-711, vol. 248, Biochemical and Biophysical Research Communications.

G. Vitale et al., "Susceptibility of Mitogen-Activated Protein Kinase Kinase Family Members to Proteolysis by Anthrax Lethal Factor", 2000, pp. 739-745, vol. 352, Biochem. J.

D. J. Weber et al., "In Vitro Susceptibility of *Bacillus* spp. to Selected Antimicrobial Agents", 1988, pp. 642-645, vol. 32, No. 5, Antimicrobial Agents and Chemotherapy.

E. Helgason et al., "*Bacillus anthracis, Bacillus cereus*, and *Bacillus thuringiensis*-One Species on the Basis of Genetic Evidence", 2000, pp. 2627-2630, vol. 66, No. 6, Applied and Environmental Microbiology.

N. S. Duesbery et al. "Proteolytic Inactivation of MAP-Kinase-Kinase by Anthrax Lethal Factor" 1998, pp. 734-737, vol. 280, Science.

S. E. Hammond et al., "Lehtal Factor Active-Site Mutations Affect Catalytic Activity in Vitro", 1998, pp. 2374-2378, vol. 66, No. 5, Infection and Immunity.

R. T. Cummings et al., "Peptide-based fluorescence Resonance Energy Transfer Assay for *Bacillus anthracis* Lethal Factor Protease", 2002, pp. 6603-6606, vol. 99, No. 10, PNAS.

M. Doganay et al., "Antimicrobial Susceptibility of *Bacillus anthracis*" 1991, pp. 333-335, vol. 23, Scand J. Infect Dis.

A. Scozzafava et al., "Carbonic Anhydrase and Matrix Metalloproteinase Inhibitors: Sulfonylated Amino Acid Hydroxamates with MMP Inhibiotry Properties Act as Efficient Inhibitors of CA Isozymes I, II, and IV, and N-Hydroxysulfonamides Inhibit both These Zinc Enzymes", 2001, pp. 1016, vol. 44, J. Medicinal Chemistry. Chemical Abstract 137:194969.

S. M. Dankwardt et al., "Amino Acid Derived Sulfonamide Hydroxamates as Inhibitors of Procollagen C-Proteinase: Solid-Phase Synthesis of Ornithine Analogues", 2001, pp. 2085-2088, vol. 11 (16), Bioorganic & Medicinal Chemistry Letters. Chemical Abstract 135:344719.

S. Pikul et al., "Potent and Selective Carboxylic Acid-Based Inhibitors of Matrix", 2001, pp. 2499-2502, vol. 44 (16), J. of Medicinal Chemistry. Chemical Abstract 135:210918.

M. Ikeda et al., "Inhibition of Gelatinolytic Activity in Tumor Tissues by Synthetic Matrix Metalloproteinase Inhibitor", 2000, pp. 3290-3296, vol. 6(8), Clinical Cancer Research. Chemical Abstract 134:125645.

P. M. O'Brien et al., "Structure-Activity Relationships and Pharmacokinetic Analysis for a Series of Potent, Systemically Available Biphenylsulfonamide Matrix", 2000, pp. 156-166, vol. 43(2), J. of Medicinal Chemistry. Chemical Abstract 132:231496.

V. G. Reddy, "A Novel, Simple and Practical Protocol for N-protected-alpha-amino Hydroxamic Acids", 1999, pp. 3613-3619, vol. 29 (20), Synthetic Communications. Chemical Abstract 131:286005.

T. Brennan, "Two-Dimensional Parallel Array Technology as a New Approach to Automated Combinatorial Solid-Phase Organic Synthesis", 1998, pp. 33-45, vol. 61(1), Biotechnology and Bioengineering. Chemical Abstract 129:29436.

Y. Tamura et al., "Highly Selective and Orally Active Inhibitors of Type IV Collagenase", 1998, pp. 640-619, vol. 41(4), J. of Medicinal Chemistry. Chemical Abstract 128:188290.

J. Hansel et al., "Ozazoline Formation via a Palladium-Catalyzed Cyclization: a Direct, Stereoselective Approach to Cis-5-Amino-2-Cyclopenten-l-ol Derivatives", 1995, pp. 2913-2916, Tetrahedron Letters. Chemical Abstract 123:227656.

S. Natelson et al., "Preparation of D-, DL-, and L-Homoserine Lactone from Methionine", 1989, pp. 226-232, vol. 40(2), Microchemical J. Chemical Abstract 112:179786.

N. Yoneda et al., "Reaction of L-alpha-tosylamido-Bet-Propiolactone. I. Synthesis, Reactions with Amines, and Derivation to L-Serine", 1969, pp. 98-103, vol. 89(1), Yakugaku Zasshi. Chemical Abstract 70:88228.

K. Takahashi et al., "Phenylsulfonamide Derivative", 1998, 10-204059, Patent Abstracts of Japan.

K. Takahashi et al., "Phenylsulfonamide Derivative", 1997, 11-035557, Patent Abstracts of Japan.

F. Watanabe et al., "MMP-8 Inhibitor", 1998, 11-246527, Patent Abstracts of Japan.

U.S. Appl. No. 11/006,335, Hermes, (unpublished).

Armelle Menard et al., 320 Biochem. J. 687-91 (1996).

W.L. Shoop et al., 102(22) PNAS (2005).

Ansu Agrawal et al., 424 Nature 329-34 (2003).

Paolo Ascenzi et al., 5531 FEBS Letters 384-88 (2002).

R.J. Cherney et al., 46 J. Med. Chem. 1811-23 (2003).

J. Inoue et al., 46 J. Med. Chem. 868-71 (2003).

H.B. Milne et al., 79 J. Am. Chem. Soc. 645-48 (1857).

T. Benicori et al., 65 J. Org. Chem. 2043-47 (2000).

D. Liu et al., 4 Org. Lett. 4471-74 (2002).

A. Togni et al., 116 J. Am. Chem. Soc. 4062-66 (1994).

K. Mashima et al., J. Chem. Soc. Chem. Comm. 1208-10 (1989).

D.C. Wetter et al., 91(5) The American Journal of Public Health, 710-716 (2001).

S. Shafazand et al., 116, Chest, 1369-1376 (1999).

Advisory Action Before the Filing of An Appeal Brief dated May 6, 2008 for U.S. Appl. No. 11/006,335, filed Dec. 7, 2004.

Amendment filed in Response to Office Action dated May 6, 2008 for U.S. Appl. No. 11/006,335, filed Dec. 7, 2004.

Hidemase Takaya et al., *New chiral ruthenium complexes for asymmetric catalytic hydrogenations*, 62(6) *Pure & Applied Chemistry* 1135-38 (1990).

* cited by examiner

COMPOUNDS USEFUL IN THE TREATMENT OF ANTHRAX AND INHIBITING LETHAL FACTOR

CROSS REFERENCE TO RELATED APPLICATIONS

This application is the National Stage of International Application No. PCT/US2003/016336 filed May 23, 2003 which claims the benefit under 35 U.S.C. 119(e) of U.S. Provisional Application No. 60/383,996 filed on May 29, 2002.

BACKGROUND OF THE INVENTION

The references cited throughout the present application are not admitted to be prior art to the claimed invention.

Anthrax is a bacterial infection produced by *Bacillus anthracis*. *Bacillus anthracis* endospores can enter the body through skin abrasions, inhalation, or ingestion. *Bacillus anthracis* produces an anthrax toxin that is often lethal. (Dixon et al., (1999) *N. Engl. J. Med.* 341, 815-26.)

Anthrax toxin consists of three proteins, a receptor-binding component designated protective antigen, and two enzymatic components termed edema factor and lethal factor ("LF"). (Mock et al., (2001) *Annu. Rev. Microbiol.* 55, 647-71.) Lethal factor is a zinc-dependent metalloprotease that appears to exert toxic affects by cleaving mitogen-activated protein kinase kinases (MKKs). (Vitale et al., (1998) *Biochem. Biophys. Res. Commun.* 248, 706-11, Vitale et al., (2000) *Biochem. J.* 352 Pt 3, 739-45, Duesbery et al., (1998) *Science* 280, 734-7, Duesbery et al., International Publication No. WO 99/50439, International Publication Date Oct. 7, 1999.)

Vitale and co-workers have used microsequencing to identify the site in different MKKs that are cleaved by lethal factor. (See Table 1, Vitale et al., (2000) *Biochem. J.* 352 Pt 3, 739-45.) Lethal factor cleavage of different MKKs occurred within the N-terminal region preceding the kinase domain. Alignment of the sequences flanking the cleavage site revealed some consensus motifs: a hydrophobic residue in position P2 and P1', and at least one basic residue between P4 and P7. (Vitale et al., (2000) *Biochem. J.* 352 Pt 3, 739-45.)

Lethal factor has been indicated to cleave synthetic peptides in vitro. (Hammond et al., (1998) *Infect. Immun.* 66, 2374-8.) In vitro cleavage was inhibited by 1,10-phenanthroline or 10 mM EDTA, both of which chelate zinc.

*Bacillus anthracis* is a spore forming gram-positive *bacillus*, which is the etiologic agent of anthrax. Anthrax is a disease that can be found globally in temperate zones (e.g. South and Central America, South and East Europe, Asia, Africa, Middle East, and Caribbean) and is transmissible to humans through handling or consumption of contaminated animal products (e.g. eating undercooked meat from infected animals). Wildlife mammals such as deer, wildebeest, elephants, and domesticated livestock, such as goats, sheep, cattle, horses, and swine are at high risk for contracting the disease. Contraction generally occurs from grazing on contaminated land, eating contaminated feed or drinking from contaminated water holes. *Bacillus anthracis* spores can remain viable in soil for many years. See Helgason et al., *Applied and Environmental Microbiology* 2000 66(6) pgs. 2627-2630; Wber et al., *Antimicrob Agents and Chemotherapy* 1988 32(5): 642-645; and Doganay et al., *Scand. J. Inf. Dis.* 1991 23:333-335 for further discussion of *Bacillus anthracis*.

In humans three forms of anthrax infections can occur, cutaneous, gastro-intestinal and inhalational. With the cutaneous form, infections occur when the bacterium or spore enters a cut or abrasion on the skin. See Synder, J. W., Shapiro, D. S., Gilchrist, M. J. R., et al., "Basic Diagnostic Testing Protocols for Level A Laboratories (For The Presumptive Indentification of *Bacillus anthracis*)" at www.ban.asm.1a.cp.102401f, Oct. 24, 2001, pgs. 1-20 and Dixon, et al., *NEJM* 341: 815-826 Sep. 9, 1999 Number 11. Symptoms of the skin infection are generally raised itchy bumps or bump that resembles an insect bite. Within one to two days, the bumps or bump develops into a fluid-filled vesicle, which ruptures to form a painless ulcer with a characteristic black necrotic (dying) area in the center. If left untreated, death can result, however, deaths are rare if appropriate antibiotic therapy is administered.

Gastrointestinal anthrax generally occurs from the consumption of meat contaminated with the bacterium, which results in an acute inflammation of the intestinal tract. Signs of nausea, loss of appetite, vomiting, fever, along with abdominal pain, vomiting of blood and severe diarrhea are indicative of gastrointestinal anthrax. The mortality rate for this form of human anthrax is estimated at 25%-60%.

Inhalation anthrax is most likely the result of intentional aerosol release of *Bacillus anthracis*, such as an act of bioterrorism. This form of human anthrax infection commonly has an incubation period of one to six days, with fever, malaise, fatigue, a nonproductive cough and/or mild chest discomfort sometimes being the initial signals. These initial symptoms are often followed by a short period of improvement, followed by the abrupt development of sever respiratory distress with labored breathing, perspiration and bluish skin color. Death usually occurs within 24-36 hours after the onset of respiratory distress despite aggressive treatment.

Most *Bacillus anthracis* strains are sensitive to a broad range of antibiotics. The commonly prescribed therapies today are ciprofloxacin, penicillin, or doxycycline. However, the efficacy and side effect profiles of these agents are not ideal.

While antibiotics can kill the bacteria that cause anthrax, the tripartite anthrax toxin continues to damage the body even when the bacteria themselves are dead. Therefore, there still exist the need for new and effective therapies with improved efficacy, little or no side effect and which inhibit the scissor-like ability of lethal factor to snip apart imprtant host molecules.

SUMMARY OF THE INVENTION

This invention relates to novel compounds of formula I:

FORMULA I $$\text{HO}\diagdown\underset{H}{N}\diagup\underset{\parallel}{\overset{O}{C}}\diagdown\underset{R}{\overset{H}{C}}\diagdown\underset{H}{N}\diagdown\underset{\overset{\parallel}{O}}{\overset{O}{S}}\diagdown R^1$$

or a pharmaceutically acceptable salt, enantiomer, diastereomer or in vivo hydrolysable ester or mixture thereof, wherein, $R^1$ represents $C_{6-10}$ aryl, $C_{5-10}$ heteroaryl or $C_{5-10}$ heterocyclic, said aryl, heteroaryl and heterocyclyl optionally substituted with 1 to 3 groups of $R^a$ $R^a$ represents $C_{1-6}$ alkyl, halogen, OH, aryl($C_{1-6}$)alkyl, ($C_{1-6}$) alkoxy, ($C_{1-6}$)alkoxy($C_{1-6}$)alkyl, halo($C_{1-6}$)alkyl, nitro, amino, mono- or di-N-($C_{1-6}$)alkylamino, acylamino, acyloxy, carboxy, carboxy salts, carboxy esters, carbamoyl, mono- and di-N-($C_{1-6}$)alkylcarbamoyl, ($C_{1-16}$)alkoxycarbonyl, aryloxycarbonyl, ureido, guanidino, sulphonylamino, aminosulphonyl, ($C_{1-6}$)alkylthio, ($C_{1-6}$)alkylsulphinyl, ($C_{1-6}$)alkylsulphonyl, heterocyclyl, heterocyclyl ($C_{1-6}$)alkyl; and R represents $C_{1-8}$ alkyl, $C_{3-10}$ cycloalkyl, $C_{3-10}$ heterocloalkyl, $C_{5-10}$ heteroaryl, or $C_{5-11}$ heterocyclyl, said heteroaryl and heterocyclyl optionally substituted with 1 to 3 groups of $R^a$ and said alky, optionally substituted with 1-3 groups selected from the group consisting of aryl, heterocyclyl, ($C_{1-6}$)alkylthio, cyano, heteroaryl, guanidino, ((1-aminoethyl)carbonyl)amino, ((aminomethyl)carbonyl)amino, ((2-amino)prop-2-yl) carbonyl)amino, acetamido, 4-(aminomethyl)phenyl, thio, t-butyl sulfonyl, ($C_{2-6}$)alkenylthio, ($C_{2-6}$)alkynylthio, amino, mono- or di-($C_{1-6}$) alkylamino, arylthio, heterocyclylthio, ($C_{1-6}$)alkoxy, aryl ($C_{1-6}$)alkoxy, aryl($C_{1-6}$)alkylthio, cycloalkyl, cycloalkenyl, carboxy and esters thereof, hydroxy and halogen.

This invention further relates to the use of the compounds of formula I in the treatment of anthrax and other conditions, which are related to an anthrax infection.

This and other aspects of the invention will be realized upon inspection of the invention as a whole.

DETAILED DESCRIPTION OF THE INVENTION

The present invention is directed to the compounds of formula I, and a method for treating anthrax or inhibiting lethal factor by administration, preferably intravenous or intra-muscular, of a composition containing a compound of formula I and a pharmaceutically acceptable carrier.

The invention is described herein in detail using the terms defined below unless otherwise specified.

When any variable (e.g. aryl, heterocycle, $R^1$, R etc.) occurs more than one time in any constituent, its definition on each occurrence is independent at every other occurrence. Also, combinations of substituents/or variables are permissible only if such combinations result in stable compounds.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When the alkyl group is said to be substituted with an alkyl group, this is used interchangeably with "branched alkyl group".

Preferably, alkenyl is $C_2$-$C_6$ alkenyl.

Preferably, alkynyl is $C_2$-$C_6$ alkynyl.

Cycloalkyl is a specie of alkyl containing from 3 to 15 carbon atoms, unless otherwise specified, without alternating or resonating double bonds between carbon atoms. It may contain from 1 to 4 rings that are fused. Examples of cycloalkyl groups are cyclopropyl, cyclobutyl, cyclopentyl, cyclohexyl, and cycloheptyl. Heterocycloalkyl is intended to mean cycloalkyl ring groups which consists of carbon atoms and from one to four heteroatoms selected from the group consisting of N, O, and S, and including any bicyclic. Said heterocycloalkyl can optionally be substituted with 1 to 3 groups of $R^a$ described herein. Examples of Heterocycloalkyls are oxane, methyloxane, dioxane, pyran, thiolane, piperidine, pyrrolidine, aziridine, azetidine, etc.

Alkoxy refers to $C_1$-$C_6$ alkyl-O—, with the alkyl group optionally substituted as described herein. Examples of alkoxy groups are methoxy, ethoxy, propoxy, butoxy and isomeric groups thereof.

Halo is short for halogen and refers to chloride, fluoride, bromide and iodide.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocyclyl or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

Preferably, heterocycle is selected from 2-azepinonyl, benzimidazolyl, 2-diazapinonyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzofuranyl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl.

In one embodiment of this invention relating to the compounds of formula I R is a heterocycloalkyl and all other variables are as originally described.

In another embodiment of this invention relating to the compounds of formula I R is a heteroaryl and all other variables are as originally described.

In still another embodiment of this invention relating to the compounds of formula I $R^1$ is a phenyl group optionally substituted with 1-3 groups of $R^a$ and R is a heterocycloalkyl, or heteroaryl group.

In yet another embodiment of the invention relating to the compounds of formula I $R^1$ is a phenyl group substituted with 1 to 3 groups of methoxy, halogen, methyl, ethyl, propyl, butyl, napthyl, 5-(2-pyridyl)thiophen-2-yl or a mixture thereof, and R a heterocycloalkyl or heteroaryl.

In yet another embodiment of this invention relating to the compounds of formula Ia R is a heterocycloalkyl and all other variables are as originally described.

In another embodiment of this invention relating to the compounds of formula Ia R is a heteroaryl and all other variables are as originally described.

In another embodiment of this invention relating to the compounds of formula Ia R is a $C_{1-4}$ alkyl and all other variables are as originally described.

In still another embodiment of this invention relating to the compounds of formula Ia $R^1$ is a phenyl group optionally substituted with 1-3 groups of $R^a$ and R is an alkyl, heterocycloalkyl, or heteroaryl group.

In yet another embodiment of the invention relating to the compounds of formula Ia $R^1$ is a phenyl group substituted with 1 to 3 groups of methoxy, halogen, methyl, ethyl, propyl, butyl, napthyl, 5-(2-pyridyl)thiophen-2-yl or a mixture thereof, and R is an alkyl, heterocycloalkyl or heteroaryl.

Another embodiment of this invention relates to a pharmaceutical composition comprising a compound of formula I and a pharmaceutically acceptable carrier.

Another embodiment of this invention involves the use of a compound of formula I for the production of a medicament for the treatment or prophylaxis of anthrax and conditions related thereto. Still another embodiment involves the use of a compound of formula I for the production of a medicament for inhibiting lethal factor.

The compounds of formula I may be combined with one or more known drugs selected from clinically useful antibacterial agents (for example other beta-lactams or aminoglycosides), inhibitors of beta-lactamase, renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids (for example see EP-A-178911) which reduce adverse effects on the kidney. Examples of drugs that can be combined with the compounds of formula I are imipenem, meropenem, vancomycin, cilastatin, cefoxitin, penicillin, clavulanic acid, probenecid, tetracycline, ciprofloxacin, norfloxacin or a mixture thereof. It is preferred that when imipenem is used as a drug it is used in combination with cilastatin (said combination is marketed as PRIMAXIN®).

Suitable pharmaceutically acceptable salts of the compounds used in this invention include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. Preferred pharmaceutically acceptable salts are sodium and potassium salts.

In vivo hydrolysable esters are those pharmaceutically acceptable esters that hydrolyze in the human body to produce the parent compound. Such esters can be identified by administering, e.g. intravenously to a test animal, the compound under test and subsequently examining the test animal's body fluids. Suitable in vivo hydrolysable esters for carboxy include C1-6alkoxymethyl esters for example methoxymethyl, C1-6 alkanolyloxymethyl esters for example pivaloyloxymethyl, phthalidyl esters and the additional esters disclosed in U.S. Pat. No. 5,478,820, which is herein incorporated by reference in its entirety.

Compounds used in this invention are:

N-t-butoxy-2(R)-[(4-fluoro-3-methylphenylsulfonyl)] amino-3-methylbutyramide;

N-hydroxy-2(R)-[(4-fluoro-3-methylphenylsulfonyl)] amino-3-methylbutyramide;

N-t-butoxy-2(R)-[(4-fluoro-3-methylphenylsulfonyl)] amino-2-(4'-tetrahydropyranyl)-acetamide;

N-hydroxy-2(R)-[(4-fluoro-3-methylphenylsulfonyl)] amino-2-(4'-tetrahydropyranyl)-acetamide;

N-hydroxy-2(R)-[(4-fluoro-3-methylphenylsulfonyl)] amino-3-(S)-cyclopropylbutyramide; and pharmaceutically acceptable salts, enantiomers, diastereomers or in vivo hydrolysable esters or mixtures thereof.

Additional compounds of this invention are disclosed in Table 1:

TABLE 1

| Example # | R1 | R2 |
|---|---|---|
| 3 | (chain with NH, N-H, NH2 guanidine group) | 4-fluoro-3-methylphenyl |
| 4 | (chain with NH, N-H, NH2 guanidine group) | 4-fluorophenyl |

TABLE 1-continued
| Example # | R1 | R2 |
|---|---|---|
| 5 | 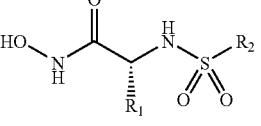 | 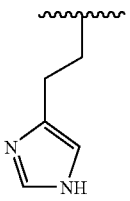 |
| 6 | 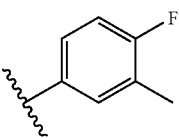 | 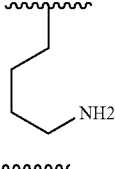 |
| 7 | 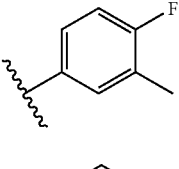 | 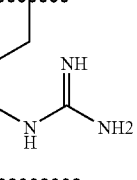 |
| 8 | 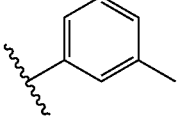 | 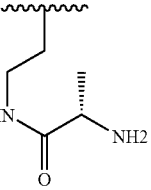 |
| 9 | 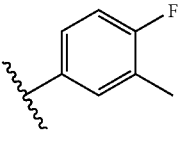 | 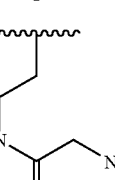 |
| 10 | 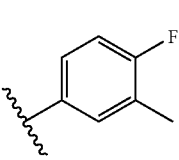 | 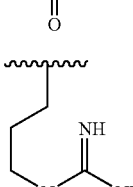 |
| 11 | 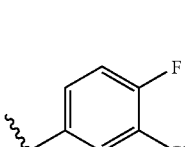 | 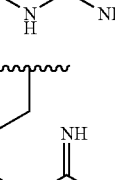 |
| 12 | 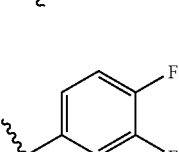 | 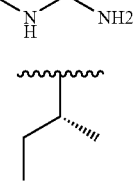 |
| 13 | 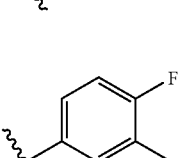 | 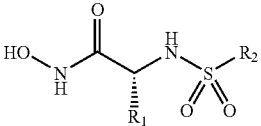 |
| 14 | 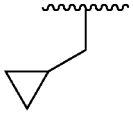 | 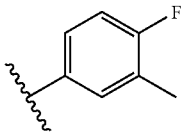 |
| 15 | 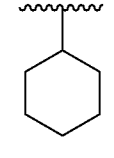 | 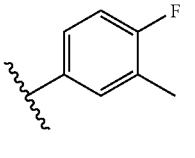 |
| 16 | 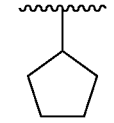 | 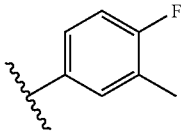 |
| 17 | 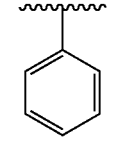 | 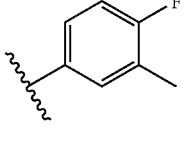 |
| 18 | 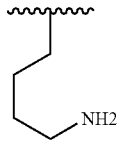 | 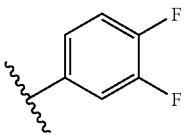 |
| 19 | 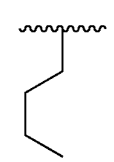 | 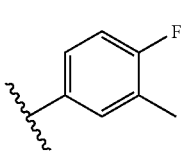 |
| 20 | 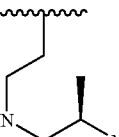 | 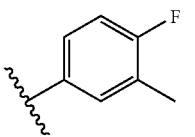 |

TABLE 1-continued

| Example # | R1 | R2 |
|---|---|---|
| 21 | -CH2CH2NHC(O)C(CH3)2NH2 | 4-fluoro-3-methylphenyl |
| 22 | -(CH2)3NHC(=NH)NH2 | phenyl |
| 23 | -(CH2)4NHC(O)CH2NH2 | 4-fluorophenyl |
| 24 | -CH2CH3 | 4-fluoro-3-methylphenyl |
| 25 | -CH(CH3)CH2CH3 | 4-fluoro-3-methylphenyl |
| 26 | cyclopropyl | 4-fluoro-3-methylphenyl |
| 27 | -CH2CH(CH3)2 extended (isopentyl) | 4-fluoro-3-methylphenyl |
| 28 | -(CH2)3NHC(=NH)NH2 | 3,4-methylenedioxyphenyl |
| 29 | -CH2NHC(O)C(CH3)2NH2 | 4-fluoro-3-methylphenyl |
| 30 | -CH2-cyclopropyl | 4-fluorophenyl |
| 31 | -(CH2)3NHC(=NH)NH2 | 3-fluorophenyl |
| 32 | -(CH2)3NHC(=NH)NH2 | 3-methoxyphenyl |
| 33 | -CH2-cyclopropyl | 4-fluorophenyl |
| 34 | -CH2NHC(O)CH2NH2 | 4-fluoro-3-methylphenyl |
| 35 | -(CH2)3NHC(=NH)NH2 | 4-methoxyphenyl |
| 36 | cyclopentyl | 4-fluorophenyl |

TABLE 1-continued

| Example # | R1 | R2 |
|---|---|---|
| 37 | -(CH2)3-NH-C(=NH)-NH2 | 3-Cl-phenyl |
| 38 | -(CH2)3-NH2 | 4-F-phenyl |
| 39 | -CH2-NH-C(=O)-CH(NH2)-CH3 | 4-F-3-methyl-phenyl |
| 40 | -(CH2)3-NH-C(=NH)-NH2 | 3,5-diCl-phenyl |
| 41 | -(CH2)3-NH-C(=O)-CH(NH2)-CH3 | 4-F-phenyl |
| 42 | -(CH2)4-NH2 | 3,5-diCl-phenyl |
| 43 | -cyclopentyl | 3-methyl-phenyl |
| 44 | -cyclohexyl | 3,4-diF-phenyl |
| 45 | -CH2-NH-C(=O)-CH(NH2)-CH3 | 4-F-3-methyl-phenyl |
| 46 | -(CH2)3-NH-C(=NH)-NH2 | 3,4-diCl-phenyl |
| 47 | -CH3 | 4-F-3-methyl-phenyl |
| 48 | -(CH2)4-NH2 | 3-Cl-phenyl |
| 49 | -(CH2)4-NH2 | 4-methyl-phenyl |
| 50 | -(CH2)3-NH-C(=NH)-NH2 | 2,5-diCl-thiophen-3-yl |
| 51 | -CH2-cyclopropyl | 3-methyl-phenyl |
| 52 | -cyclohexyl | 4-F-phenyl |

TABLE 1-continued

Structural formula: HO-NH-C(=O)-CH(R1)-NH-S(=O)2-R2

| Example # | R1 | R2 |
|---|---|---|
| 53 | cyclopentylmethyl | 4-fluoro-3-methylphenyl |
| 54 | isobutyl | 4-fluoro-3-methylphenyl |
| 55 | neopentyl | 4-fluoro-3-methylphenyl |
| 56 | 3-aminopropyl | 3-methylphenyl |
| 57 | cyclopentyl | 3,4-difluorophenyl |
| 58 | phenyl | 4-fluorophenyl |
| 59 | 4-aminobutyl | 4-methoxyphenyl |
| 60 | indan-2-yl | 4-fluorophenyl |
| 61 | 3-guanidinopropyl | 4-chlorophenyl |
| 62 | cyclopropylmethyl | phenyl |
| 63 | 3-guanidinopropyl | 3,5-difluorophenyl |
| 64 | tetrahydropyran-4-yl | 4-fluorophenyl |
| 65 | 4-acetamidobutyl | 3-methylphenyl |
| 66 | cyclohexyl | 3,5-dichlorophenyl |
| 67 | cyclopropylmethyl | 3-chloro-4-fluorophenyl |
| 68 | pentyl | 4-fluorophenyl |

TABLE 1-continued

| Example # | R1 | R2 |
|---|---|---|
| 69 | -(CH2)4-NHC(O)CH3 | 4-F-phenyl |
| 70 | cyclopentyl | 4-OMe-phenyl |
| 71 | cyclopropylmethyl | 3-F-phenyl |
| 72 | -(CH2)2-NHC(O)CH(NH2)CH3 | 4-F-phenyl |
| 73 | -(CH2)4-NHC(O)CH(NH2)CH3 | 4-F-phenyl |
| 74 | tetrahydropyran-4-yl | 3,4-diF-phenyl |
| 75 | isopropyl | 3-Me-phenyl |
| 76 | indan-2-yl | 4-OMe-phenyl |
| 77 | -(CH2)3-NHC(=NH)NH2 | 4,5-diCl-thien-2-yl |
| 78 | tetrahydropyran-4-yl | 3,5-diCl-phenyl |
| 79 | cyclopentyl | 3-Cl-phenyl |
| 80 | n-butyl | 3-Me-phenyl |
| 81 | n-butyl | 4-F-phenyl |
| 82 | isobutyl | 3-Me-phenyl |
| 83 | isobutyl | 4-F-phenyl |
| 84 | cyclohexyl | 4-OMe-phenyl |
| 85 | cyclopropyl | 4-F-phenyl |

TABLE 1-continued

| Example # | R1 | R2 |
|---|---|---|
| 86 | 2,3-dihydro-1H-inden-2-yl | 3-chlorophenyl |
| 87 | 3-cyanopropyl | 4-fluoro-3-methylphenyl |
| 88 | cyclopropylmethyl | 3,5-dichlorophenyl |
| 89 | 2-(1H-imidazol-4-yl)ethyl | 4-fluorophenyl |
| 90 | isobutyl | 4-fluorophenyl |
| 91 | cyclohexyl | 3-chlorophenyl |
| 92 | (S)-sec-butyl | 3-chlorophenyl |
| 93 | neopentyl | 4-fluoro-3-methylphenyl |
| 94 | (S)-sec-butyl | 4-methoxyphenyl |
| 95 | 4-(alaninamido)butyl | 3-methylphenyl |
| 96 | 4-(alaninamido)butyl | 4-fluorophenyl |
| 97 | cyclopentylmethyl | 4-fluorophenyl |
| 98 | pentyl | 3-chlorophenyl |
| 99 | 2-(alaninamido)ethyl | 4-fluorophenyl |
| 100 | 2-(2-amino-2-methylpropanamido)ethyl | 4-fluorophenyl |
| 101 | 2-(methylthio)ethyl | 4-fluorophenyl |

TABLE 1-continued

| Example # | R1 | R2 |
|---|---|---|
| 102 | -CH2CH2CH2CH2-NH-C(O)-CH2-NH2 | 3-methylphenyl |
| 103 | isopropyl | 3,4-difluorophenyl |
| 104 | -CH2CH2CH2CH2-NH-C(O)-CH2-NH2 | 4-fluorophenyl |
| 105 | 4-piperidinyl | 3-methylphenyl |
| 106 | cyclopropylmethyl | 4-methoxyphenyl |
| 107 | -CH2CH2CH2-NH-C(=NH)-NH2 | 3-cyanophenyl |
| 108 | 2-cyclohexylethyl | 4-fluorophenyl |
| 109 | (4-piperidinyl)methyl | 4-fluorophenyl |
| 110 | -CH2-NH-C(O)-C(CH3)2-NH2 | 4-fluorophenyl |
| 111 | -CH2CH2CH2CH2-NH-C(O)-CH(CH3)-NH2 | 3-methylphenyl |
| 112 | isobutyl | 3-chloro-4-fluorophenyl |
| 113 | -CH2CH2CH2-NH-C(O)-CH2-NH2 | 3-methylphenyl |
| 114 | isobutyl | 3,5-dichlorophenyl |
| 115 | isopropyl | 3-bromophenyl |
| 116 | isobutyl | 3-chlorophenyl |
| 117 | phenyl | 3-chlorophenyl |

TABLE 1-continued structure

| Example # | R1 | R2 |
|---|---|---|
| 118 | sec-butyl (methyl, ethyl) | 3-methoxyphenyl |
| 119 | cyclopropyl | 3,5-dichlorophenyl |
| 120 | -CH2-NH-C(O)-CH2-NH2 | 4-fluorophenyl |
| 121 | isobutyl | 5-chlorothiophen-2-yl |
| 122 | -(CH2)3-NH2 (4-aminobutyl) | 3,5-dichlorophenyl |
| 123 | neopentyl | 4-fluorophenyl |
| 124 | ethyl | 3-chlorophenyl |
| 125 | 2-cyclohexylethyl | 3-methylphenyl |
| 126 | cyclopropylmethyl | benzo[1,3]dioxol-5-yl |
| 127 | 4-(aminomethyl)benzyl | 3-methylphenyl |
| 128 | isobutyl | 4-methoxyphenyl |
| 129 | ethyl | 3-chlorophenyl |
| 130 | tetrahydropyran-4-yl | 3-fluorophenyl |
| 131 | isobutyl | phenyl |
| 132 | (1-methylcyclopropyl)methyl | 4-fluoro-3-methylphenyl |
| 133 | -CH2-CH2-S(O)2-tBu | 3-methylphenyl |
| 134 | (R)-1-hydroxyethyl | 3-chlorophenyl |
| 135 | thiophen-3-ylmethyl | 4-fluorophenyl |

TABLE 1-continued

![Structure: HO-NH-C(=O)-CH(R1)-NH-S(=O)2-R2]

| Example # | R1 | R2 |
|---|---|---|
| 136 | -CH2-SH | 4-F-phenyl |
| 137 | -CH(CH3)2 (isopropyl) | 5-(isoxazol-3-yl)thiophen-2-yl |
| 138 | -CHF-CH2F (or -CH2-CHF2) | 3-methylphenyl |
| 139 | -CH(CH3)2 (isopropyl) | 2,5-dichlorothiophen-3-yl |
| 140 | -CH2-(piperidin-3-yl) | 3-methylphenyl |
| 141 | -(CH2)3-NH-C(=NH)-NH2 | 4-cyanophenyl |
| 142 | -CH2-(1H-imidazol-4-yl) | 4-F-phenyl |
| 143 | -CH2-(thiophen-2-yl) | 3,5-dichlorophenyl |

TABLE 1-continued

![Structure: HO-NH-C(=O)-CH(R1)-NH-S(=O)2-R2]

| Example # | R1 | R2 |
|---|---|---|
| 144 | -CH2-(1H-indol-3-yl) | 4-methoxyphenyl | and pharmaceutically acceptable salts, enantiomers, diastereomers or in vivo hydrolysable esters or mixtures thereof.

Still other compounds of this invention are disclosed in Table 2:

TABLE 2

![Structure: HO-NH-C(=O)-CH(NH-S(=O)2-(4-F-3-methylphenyl))-CH(R2)-O-R1]

| Example # | R1 | R2 |
|---|---|---|
| 146 | cyclopentyl | Me |
| 147 | ethyl | Me |
| 148 | n-butyl | Me |
| 149 | -CH2-CH2-NH2 | H |
| 150 | -CH2-cyclopropyl | Me |
| 151 | -CH2-CH(CH3)-CH2-CH3 (or isopentyl) | Me |
| 152 | benzyl | Me |

TABLE 2-continued

| Example # | R1 | R2 |
|---|---|---|
| 153 | cyclobutylmethyl | Me | and pharmaceutically acceptable salts, enantiomers, diastereomers or in vivo hydrolysable esters or mixtures thereof.

Preferred compounds used in this invention are:
N-t-butoxy-2(R)-[(4-fluoro-3-methylphenylsulfonyl)]amino-3-methylbutyramide;
N-hydroxy-2(R)-[(4-fluoro-3-methylphenylsulfonyl)]amino-3-methylbutyramide;
N-t-butoxy-2(R)-[(4-fluoro-3-methylphenylsulfonyl)]amino-2-(4'-tetrahydropyranyl)-acetamide;
N-hydroxy-2(R)-[(4-fluoro-3-methylphenylsulfonyl)]amino-2-(4'-tetrahydropyranyl)-acetamide;
N-hydroxy-2(R)-[(4-fluoro-3-methylphenylsulfonyl)]amino-3-(S)-cyclopropylbutyramide; and pharmaceutically acceptable salts, enantiomers, diastereomers or in vivo hydrolysable esters or mixtures thereof.

In order to use a compound of formula I or a pharmaceutically acceptable salt, enantiomer, diastereomer or in vivo hydrolysable ester or mixture thereof for the therapeutic treatment of mammals, including humans, in particular in treating anthrax, or inhibting lethal factor it is normally formulated in accordance with standard pharmaceutical practice as a pharmaceutical compositon.

The compounds used in the instant invention can be administered in a therapeutically effective amount intravaneously, subcutaneously, intramuscularly or any other method known to those skilled in the art (e.g., rectal, oral, parenteral). A suitable pharmaceutical composition used in this invention is one, which is made for sterile injection containing between 1 and 50% w/w of the compounds used in this invention.

Suitable subjects for the administration of the formulation of the present invention include primates, man and other animals, particularly man and domesticated animals such as cats, rabbits and dogs.

The following non-limiting examples, given by way of illustration, is demonstrative of the present invention, that the compounds used in this invention are useful for treating anthrax and inhibiting lathal factor.

Definition of terms are:
HOBT—hydroxybenzotriazole
DMF—dimethylformamide
DIEA—diisopropylethylamine
TMSONH2—O-trimethylsilylhydroxylamine
PyBOP—bnezotrizole-1-yl-oxy-tris-pyrrolidino-phosphonium hexafluorophosphate
TFA—trifluoroacetic acid
HPLC—high performance liquid chromatography
DCM—dichloromethane
EDC—1-(3-dimethylaminopropyl)-3-ethylcarbodiimide
THF—tetrahydrofuran
DIC—N,N'-diisopropylcarbodiimide
MDF—dimethylformamide
DMAP—4-dimethylaminopyridine
NMP—1-methyl-2-pyrrolidinone
EDTA—ethylenediaminetetraacetic acid

EXAMPLE 1

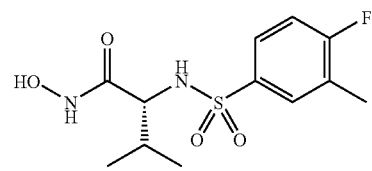

N-t-butoxy-2(R)-[(4-fluoro-3-methylphenylsulfonyl)]amino-3-methylbutyramide (1.8 g, 4.99 mmol) was dissolved in 75 ml of anhydrous dichloro-ethane containing ethanol (0.30 ml, 5 mmol) at 0° C. Hydrogen chloride gas was bubbled in for 30 min. The flask was closed with a septum and reaction mixture stirred for 2 days. After the solvent was removed on a rotavap, the residue was dissolved in methanol (1~2 ml), and diluted with DCM (20 ml). The crystals formed were collected and washed with more DCM to give, after vacuum drying, N-hydroxy-2(R)-[(4-fluoro-3-methylphenylsulfonyl)]amino-3-methylbutyramide. NMR (500 MHz, $CD_3OD$) δ: 0.86 (d, 3H), 0.91 (d, 3H), 1.86 (m, 1H), 2.30 (d, 3H), 3.30 (d, 1H), 7.16 (t, 1H), 7.67 (m, 1H), 7.72 (m, 1H).

The starting material for example 1 was prepared as follows:

D-Valine (1.39 g, 11.9 mmol) was dissolved in 80 ml of dioxane/water (1:1) containing $K_2CO_3$ (3.3 g, 24 mmol). A solution of 4-fluoro-3-methylphenyl-sulfonylchloride (10 mmol) in dioxane (4 ml) was dropped in with good stirring. The reaction mixture was stirred at room temperature for 30 min. Ethylacetate (80 ml), 1N HCl (50 ml) was added. The organic layer was washed with 1N HCl 2 times, and extracted with 5% $K_2CO_3$ (3×25 ml). The combined base extracts was acidified and extracted with ethylaceate (80 ml). The organic layer was washed with brine (2×), dried over $Na_2SO_4$. The solvent was removed on rotavap, and residue tritrated with hexane. The resulting solid was dried to give 2(R)-[(4-fluoro-3-methylphenyl-sulfonyl)]amino-3-methylbutyric acid.

2(R)-[(4-Fluoro-3-methylphenylsulfonyl)]amino-3-methylbutyric acid (2.64 g, 9.12 mmol) was dissolved in DCM (30 ml), followed by addition of DIEA (3.18 ml, 2 eq.) and O-t-butylhydroxylamine hydrochloride (2.3 g, 2 eq.). EDC.HCl (2.1 g, 1.2 eq.) was then added portionwise as solid. More EDC (0.6, 0.5 eq.) was added after 40 min and the reaction was stirred for another 30 min. The solvent was removed on a rotavap at room temperature, and residue was partitioned with ethylacetate (80 ml), 1N HCl (50 ml). The organic layer was washed with 1N HCl, brine, and dried over $Na_2SO_4$. The crude product was flash column purified with 5% to 12% ethylacetate in DCM gradient solvent to give product N-t-butoxy-2(R)-[(4-fluoro-3-methylphenylsulfonyl)]amino-3-methylbutyramide as a white foam. TLC (1:10 ethylaceate:DCM) Rf 0.16. NMR (500 MHz, CD$_3$OD) δ: 0.89 (d, 3H), 0.90 (d, 3H), 1.08 (s, 9H), 1.86 (m, 1H), 2.30 (d, 3H), 3.44 (d, 1H), 7.18 (t, 1H), 7.70 (m, 1H), 7.77 (m, 1H).

EXAMPLE 2

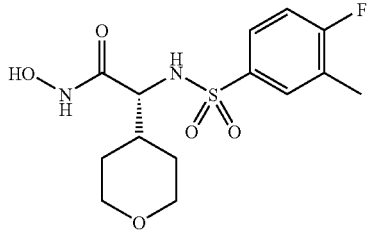

Example 2, N-hydroxy-2(R)-[(4-fluoro-3-methylphenylsulfonyl)]-amino-2-(4'-tetrahydropyranyl)-acetamide, was prepared from D-4'-tetrahydro-pyranylglycine in the same way as example 1. NMR (500 MHz, CD$_3$OD) δ: 1.19 (m, 1H), 1.34 (m, 1H), 1.40 (m, 1H), 1.74(m, 1H), 1.80(m, 1H), 2.32 (d, 3H), 3.31 (m, 2H), 3.37 (d, 1H), 3.90 (m, 2H), 7.18 (t, 1H), 7.65 (m, 1H), 7.72 (m, 1H).

EXAMPLE 3 TO 144

Examples 3 to 144, found in Table 1, were made on solid phase and is illustrated as follows:

Step 1. Resin Functionalization

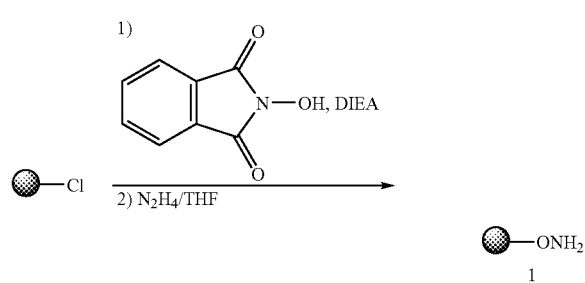

A solution of N-hydroxyphthalimide (2.8 g, 17 mmol), DIEA (3.0 ml, 17 mmol) in dichloromethane (30 ml) and DMF (15 ml) was added quickly to 4.39 g of 2-Chlorotrityl resin (1.1 mmol/g loading) in a frit fitted cartridge. The resin suspension was shaken intermittently and left on bench overnight. The resin was washed 5× with DMF, and then treated with a 40 ml of hydrazine solution (0.5 M in THF) for 2 hr. A large amount of white solid formed around the resin. It was washed with DMF-H$_2$O (1:1) 2×, DMP 4×. The hydrazine treatment was repeated once more for another 3 hours. The resin was washed with DMF-H$_2$O (1:1) 2×, DMF 4×, DCM 5×, dried in vacuum overnight to give 4.53 g of resin 1. The loading is about 1.0 mmol/g by weight change.

Step 2. Loading of Amino Acid

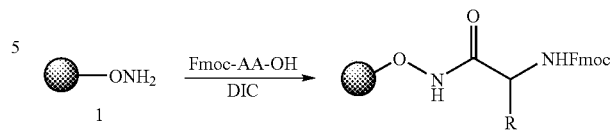

The O-anchored hydroxylamine resin 1, 500 mg (~1.0 mmol/g loading), was swelled with DCM in a frit fitted cartridge and drained. A solution of Fmoc-D-allo-isoleucine (530 mg, 1.5 mmol, 3 eq.), DIC (0.120 ml, 0.75 mmol, 1.5 eq.) in 3 ml of DMF was added. The cartridge was shaken briefly and left on bench for 1 hr. Another dose of DIC (0.04 ml, 0.25 mmol, 0.5 eq.) was added. After another hour, the resin was washed with DMF 4×, DCM 4× and vacuum dried overnight to give resin 2. The approximate loading is 0.70 mmol/g by weight gain.

Step 3

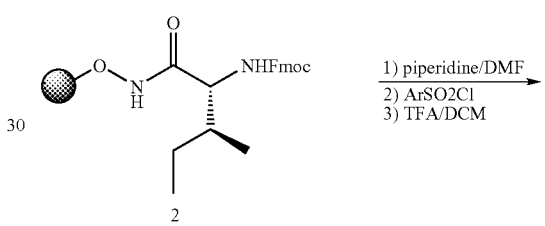

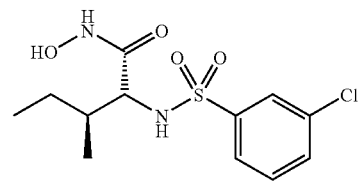

Example 25

Resin 2, 150 mg, ~0.7 mmol/g loading, was treated with 2 ml of piperidine/DMF (25%) for 2 hr. The resin was washed with MDF 3×, DCM 3×. A solution of DIEA (73 ul, 0.42 mmol, 4 eq.) in THF-DCM (1:1, 0.5 ml) containing DMAP (~2 mg) was added to the resin, followed by a solution of 3-chlorophenylsulfonyl chloride (66 mg, 3 eq.) in THF-DCM (0.5 ml). After 3 hr, the resin was washed with DMF 3×, DCM 3×, and cleaved twice with 5% TFA/DCM (0.5 ml) for 30 min. The combined cleavage solution was evaporated, and the residue dissolved in CH$_3$CN:H$_2$O and purified on a reverse phase BPLC to give Example 25, N-hydroxy-2(R)-(3-chlorophenylsulfonyl)amino-3(S)-methylvaleric amide. NMR (500 MHz, CD$_3$OD) δ: 0.82 (d, d, 6H), 1.04 (m, 1H), 1.35 (m, 1H), 1.64 (m, 1H), 3.52 (d, 1H), 7.50 (t, 1H), 7.60(d, 1H), 7.76(d, 1H), 7.84 (m, 1H).

Table 1 lists structures of examples 3 to 144. As can be appreciated by the ordinary skilled artisan, Examples 4 to 144 were made, with some modification, in accordance with the description provided for example 3. Some compounds

EXAMPLE 145

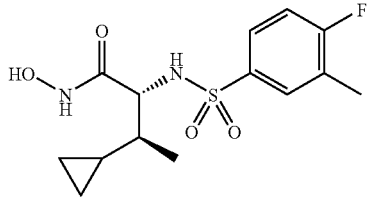

2-(R)-[(4-fluro-3-methylphenyl)sulfonyl]amino-3-(S)-cyclopropyl-butyric acid (10 mg, 31 mmol) was dissolved in DMF (0.3 ml) with HOBt (4.5 mg, 0.031 mmol), DIEA (11 ul, 0.062 mmol), O-trimethylsilylhydroxylamine (20 ul, 0.16 mmol). A solution of PYBOP (20 mg, 0.038 mmol) in DMF (0.3 ml) was added. The reaction was quenched after 30 min with $CH_3CN:H_2O$ (1:1, 5% TFA) and passed through reverse phase HPLC to give, after lyophilization, N-hydroxy-2-(R)-[(4-fluro-3-methylphenyl)sulfonyl]amino-3-(S)-cyclopropylbutyramide. NMR (500 MHz, $CD_3OD$) δ: −0.04 (m, 1H), 0.20 (m, 1H), 0.35 (m, 1H), 0.41 (m, 1H), 0.54 (m, 1H), 0.90 (d, 3H), 1.08 (m, 1H), 2.32 (d, 3H), 3.60 (d, 1H), 7.17 (t, 1H), 7.68 (m, 1H), 7.75 (m, 1H). MS: 331.1(M+H$^+$).

The starting material for example 145 was prepared as follows:

Methyl glycolate (10.4 g, 114 mmol), crotyl alcohol (100 ml, excess), was refluxed in the presence of $K_2CO_3$ (0.8 g) for 1 hr, during which time about 10 ml of the condensate was removed through a Dean-Stock trap. After diluting with hexane (100 ml), the solid was filtered through a short silica gel column (50 g), washed with 1:5 ethylacetate:hexane (250 ml). The combined filtrate and washings was concentrated to 100 ml, and was diluted again with hexane (100 ml), passed through silica gel column and washed. The solution was concentrated to ~12.5 g of oil, which was vacuum distilled to give crotyl glycolate: 9.3 g (97° C./20 mmHg) as a mixture of cis:trans (1:10). NMR (500 MHz, $CDCl_3$) δ: 1.3 (m, 3H), 4.15 (s, 2H), 4.62 (d, 2H), 5.6 (m, 1H), 5.84 (m, 1H). cis isomer: 1.71 (m, 3H), the rest peaks overlaps with trans isomer.

The above made crotyl glycolate (9.3 g, 71 mmol) in THF (10 ml) was added slowly to a solution of LiN(TMS)$_2$ (200 ml, 1.0 M) in THF (200 ml) at −78° C. After 40 min at this temperature, trimethylsilyl chloride (25.5 ml, 200 mmol) was added. The cooling bath was removed and the reaction was stirred overnight. The reaction mixture was concentrated to ~150 ml and diluted with ethylacetate (500 ml). This was washed with 2N HCl twice. The washings were back extracted with more ethylacetate. The combined organic layer was extracted with 5% $K_2CO_3$ 3×. The combined base solution was acidified with cold concentrated HCl, extracted with ethylacetate. The ethylacetate solution was washed with saturated NaCl, dried over $Na_2SO_4$. Evaporation of solvent and vacuum drying gave 2-hydroxy-3-methylpropen-4-enoic acid as a mixture of diastereomers. NMR (500 MHz, $CD_3OD$) for diastereomer 1 [(2R, 3S) and (2S, 3R)] δ: 1.02 (d, 3H), 2.60 (m, 1H), 4.05 (d, 1H), 5.02 (m, 1H), 5.09 (m, 1H), 5.87 (m, 1H); diasteteomer 2 [(2R, 3R) and (2S, 3S)] δ: 1.11(d, 3H), 2.6 (m, 1H), 4.03 (d, 1H), 5.0 (m, 1H), 5.09 (m, 1H), 5.80 (m, 1H). Diastereomeric ratio by NMR is about 7 to 1 with diasteromer 1 as the major.

The above made acid (8.5 g, 65 mmol) was disolved in dry DMF (100 ml) and DIEA (16 ml, 91 mmol). Methyl iodide (11.7 ml, 85 mmol) was added. This was stirred for 15 hr, and diluted with ethylacetate (500 ml), washed with 0.1N HCl 3×, brine 2×, dried over $Na_2SO_4$. Evaporation of solvent left Methyl 2-hydroxy-3-methylpenten-4-enoic ester. NMR (500 MHz, $CD_3OD$) for diastereomer 1 [(2R, 3S) and (2S, 3R)] δ: 1.02 (d, 3H), 2.55 (m, 1H), 3.70 (s, 3H), 4.04 (d, 1H), 5.02 (m, 1H), 5.06 (m, 1H), 5.81 (m, 1H); diasteteomer 2 [(2R, 3R) and (2S, 3S)] δ: 1.08 (d, 3H), 2.58 (m, 1H), 3.70 (s, 3H), 4.07 (d, 1H), 5.00 (m 1H), 5.06 (m, 1H), 5.80 (m, 1H).

The above made methyl ester (2.9 g, 20 mmol) was disolved in dry DCM (100 ml) with diiodomethane (8.1 ml, 100 mmol), and cooled to 0° C. A solution of diethylzinc (100 ml, 1.0 M in hexane) was added. The cooling bath was removed and the mixture was stirred under nitrogen for 3 days. A solution of $NH_4Cl$ was added to quench the reaction. The organic layer was washed with HCl 2×, brine 2×, and dried over $Na_2SO_4$. Evaporation of solvent left oil containing 70% of product methyl 2-hydroxy-3-cyclopropylbutyrate and 30% of starting material. It was used without further purification.

A solution of the above made ester (3 g, 20 mmol), pyridine (2.0 ml, 24 mmol) in dry DCM (10 ml) was slowly added to a stirred solution of Tf$_2$O (4.0 ml, 24 mmol) in DCM (100 ml) at 0° C. After 1 hr at 0° C., water was added to quench the reaction. This was then washed with dilute HCl (0.1 N), brine, and dried over $Na_2SO_4$. Evaporation of solvent gave 5.3 g of triflate as an oil. This was stirred with $NaN_3$ (2.4 g, 36 mmol) in DMF (80 ml) for 15 hr. The reaction mixture was diluted with ethylacetate (400 ml), washed with dilute HCl 3×, brine 2×, dried over $Na_2SO_4$. Evaporation of solvent lfet 2.96 g of oil. Flash column chromatography though silica gel, eluting with 5% ether in hexane gave methyl 2-azido-3-cyclopropylbutyrate as a colorless oil. The desired diastereomer 1 [(2R, 3S) and (2S, 3R)] can be isolated through preparative reverse phase HPLC eluting with $CH_3CN:H_2O$ gradient solvent. NMR (500 MHz, $CDCl_3$) for diastereomer 1 [(2R, 3S) and (2S, 3R)] δ: 0.04 (m, 1H), 0.18 (m, 1H), 0.48 (m, 2H), 0.74 (m, 1H), 1.09 (d, 3H), 1.35 (m, 1H), 3.80 (s, 3H), 3.92 (d, 1H).

The above isolated azide [(2R, 3S) and (2S, 3R)] diastereomer (400 mg, 2.2 mmol) was dissolved in MeOH (10 ml), cooled in a water bath at 20° C. Stannous chloride (860 mg, 4.4 mmol) waw added. This was stirred for 15 hr. To the reaction mixture was added with dioxane (10 m10), $K_2CO_3$ (1.5 g 10.1 mmol)/$H_2O$ (10 ml). The solid was filtered, washed with dioxane (5 ml). To the combined filtrate and washings was added a solution of 4-fluoro-3-methylphenylsulfonyl chloride (560 mg, 2.4 mmol) in dioxane (5 ml). About 30 min later, the reaction was acidified with HCl to pH 3, diluted with $CH_3CN:H_2O$. The product was isolated through preparative reverse phase HPLC (repeated injections) to Methyl 2-(4-fluoro-3-methylphenylsulfonamido)-3-cyclopropylbutyrate. Further separation through Chiralpk column AD eluting with 7% EtOH in heptane gave two enantiomers, with the desired isomer 1 (2R, 3S) eluted out first. NMR (500 M, $CD_3OD$) δ: 0.01 (m, 2H), 0.39 (m, 2H), 0.62 (m, 1H), 1.01 (d, 3H), 1.19 (m, 1H), 2.312 (d, 3H), 3.23 (s, 3H), 3.90 (d, 1H), 7.18 (t, 1H), 7.68 (m, 1H), 7.73 (m, 1H).

Methyl 2(R)-[(4-fluoro-3-methylphenyl)sulfonyl]amino-3-(S)-cyclopropyl-butyric ester (20 mg, 0.061 mmol) was dissolved in MeOH (0.2 ml), followed by addition of LiOH (8 mg, excess)/$H_2O$ (0.15 ml). After 2 hr the reaction was acidified with 1.5 ml of $CH_3CN:H_2O$ (1:1, 5% TFA) and chromatographed with reverse phase HPLC to give 2-(R)-(4-fluro-3-methylphenyl-sulfonamido)-3-(S)-cyclopropylbutyrc acid. NMR (500 MHz, $CD_3OD$) δ: −0.01

EXAMPLE 146

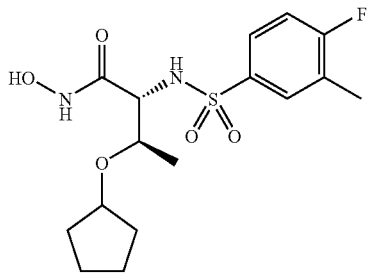

2(R)-[(4-Fluoro-3-methylphenyl)sulfonyl]amino-3(R)-cyclopentoxylbutyric acid (11 mg, 0.03 mmol) was dissolved in DMF (200 ul) with DEA (12 ul, 0.12 mmol), HOBt (8 mg, 0.06 mmol), and TMSONH$_2$ (10 ul, 0.08 mmol). A solution of PyBOP (31 mg, 0.06 mmol) in DMF (100 ul) was added. The reaction was quenched after 20 min with 5% TFA/H$_2$O, and product isolated from reverse phase HPLC to give, after lyophilization, N-hydroxy-2(R)-[(4-fluoro-3-methylphenyl)sulfonyl]amino-3(R)-cyclopentoxylbutyramide. NMR (500 MHz, CD$_3$OD) δ: 0.97 (d, 3H), 1.44-1.68 (m, 8H), 2.32 (d, J$_{H-F}$, 3H), 3.61 (d, 1H), 3.72 (m, 1H), 3.67 (m, 1H), 7.18 (m, 1H), 7.70 (m, 1H), 7.76 (m, 1H).

The starting material for example 146 was prepared as follows:

N-Trityl-D-threonine benzyl ester (2.5 g, 5.5 mmol), TEA (2.8 ml, 20 mmol) were dissolved in 100 ml of dry toluene at −50° C. A solution of sulfuryl chloride (800 ul, 8 mmol) in toluene (20 ml) was added in 15 min. The reaction was allowed to warm up to r.t. Ethylacetate (100 ml) was added and this was washed with sat. NaCl, dried over Na$_2$SO$_4$. The product was crystallized in MeOH (10 ml) to give benzyl N-trityl-3(S)-methylaziridine-2(R)-carboxylate. NMR (500 MHz, CDCl$_3$) δ: 1.37 (d, 3H), 1.64 (m, 1H), 1.95 (d, 1H), 5.15(d, J=12 Hz, 1H), 5.28(d, J=12 Hz, 1H), 7.19~7.28 (m, 12H), 7.33~7.36 (m, 1H), 7.36~7.39 (m, 3H), 7.51~7.54 (m, 4H).

Benzyl N-trityl-3(S)-methylaziridine-2(R)-carboxylate, (2.13 g, 4.92 mmol) was dissolved in 20 ml of MeOH:DCM (1:1) at 0° C., followed by addition of TEA (20 ml). After stirring at room temperature for 1 hr, the excess reagent and solvent were removed on rotavap (T<25° C.). The residue was partitioned with DCM (50 ml) and H$_2$O (100 ml). The aqueous phase was washed once with DCM, and pH was adjusted to basic with NaHCO$_3$ extracted with ethylacetate, and dried over Na$_2$SO$_4$. Removal of solvent left 650 mg of Benzyl 3(S)-methylaziridine-2(R)-carboxylate. This was dissolved in DMF (15 ml) at 0° C. TEA (2.1 ml, 15 mmol) was added, followed by Boc$_2$O (1.64 g, 7.5 mmol). The reaction was stirred at room temperature overnight. Ethylacetate (100 ml), H$_2$O (100 ml) were added, and the organic layer was washed with 10% citric acid twice, brine, and dried over Na$_2$SO$_4$. The crude product was flash column chromatographed, eluting with 5% 10% EA/hexane gradient solvent containing 0.1% TEA, to give benzyl N-Boc-3(S)-methylaziridine-2(R)-carboxylate. NMR (500 M, CD$_3$OD) δ: 1.21(d, 3H), 1.44(s, 9H), 2.82 (m, 1H), 3.21 (d, 1H), 5.2 (q, 2H), 7.30~7.38(m, 5H).

Benzyl N-Boc-3(S)-methylaziridine-2(R)-carboxylate (50 mg, 0.17 mmol), cyclopentyl alcohol (0.5 ml, 5.5 mmol) were dissolved in DCM (0.5 ml), followed by a few drops of BF$_3$.Et$_2$O. This was stirred at r.t. for 10 hr. The solvent was removed, and the residue purified through a reverse phase HPLC. The product was collected and treated with 50% TFA/DCM to give benzyl 2(R)-amino-3(R)-cyclopentoxylbutyrate triflruoroacetate. NMR (500 MHz, CD$_3$OD) δ: 1.28 (d, 3H), 1.4~1.7 (m, 8), 3.92 (m, 1H), 4.06 (d, 1H), 4.14 (dq, 1H), 5.26 (d, J=12 Hz, 1H), 5.31 (d, J=12 Hz, 1H), 7.38 (m, 3H), 7.43 (m, 2H).

Benzyl 2(R)-amino-3(R)-cyclopentoxylbutyrate triflruoroacetate (63 mg, 0.16 mmol), DIEA (174 ul, 1.0 mol), DMAP (1 mg) were dissolved in dioxane (2 ml), followed by slow addition of a solution of 4-fluoro-3-methylphenylsulfonyl chloride (~0.33 mmol) in dioxane (1 ml). After 15 min, the reaction was quenched with 5% TFA/H$_2$O, and purified through reverse phase HPLC to give benzyl 2(R)-[(4-Fluoro-3-methylphenyl)sulfonyl]amino-3(R)-cyclopentoxylbutyrate. The benzyl ester protection group was removed by hydrogenation in MeOH:EA (1 ml) with 10% Pd/C (2 mg) overnight to give 2(R)-[(4-Fluoro-3-methylphenyl)-sulfonyl]amino-3(R)-cyclopentoxylbutyric acid.

With some modification known to those skilled in the art, Examples 147 to 153 of Table 2 were made in accordance with Example 146.

Assay for Determining Lethal Factor Inhibition

The assay below is disclosed in Cummings et al., PNAS, May 14, 2002, vol. 99, no. 10, page 6603-6606 and PCT Application US03/05552, filed Feb. 21, 2003 (U.S. Patent Application Ser. No. 60/359,707, filed Feb. 25, 2002), incorporated herein by reference in their entirety. It is used to determine lethal factor inhibition after being reacted with a compound believe to be an inhibitor of lethal factor.

Lethal factor inhibitor compounds can be used to further study lethal factor activity, and those inhibitory compounds having appropriate pharmacological properties can be used to help treat or prevent Anthrax. Appropriate pharmacological properties include efficacy, metabolism and absence of unacceptable side effects.

High throughput screening for lethal factor inhibitors can be used to screen large number of compounds to identify those affecting lethal factor activity. High throughput screening is facilitated by an assay that is readily automated and utilizes low levels of purified enzyme.

Measuring Activity

Lethal factor substrates can be used in methods measuring *Bacillus anthracis* lethal factor activity and the effect of a compound on such activity. Such methods involve incubating a lethal factor substrate described herein with *Bacillus anthracis* lethal factor using an incubation medium where the *Bacillus anthracis* lethal factor is active, and can include the presence of a compound being tested. Cleavage of the substrate can be detected as a measure of *Bacillus anthracis* lethal factor activity or the effect of a compound on lethal factor activity. Measuring can be qualitative or quantitative. The lethal factor enzyme binding assay IC50 results for the compounds of this invention range from 15 uM or less. Specifically the IC50 for N-hydroxy-2(R)-[(4-fluoro-3-methylphenylsulfonyl)]amino-3-methylbutyramide and N-hydroxy-2(R)-[(4-fluoro-3-methylphenylsulfonyl)]amino-2-(4'-tetrahydopyranyl)-acetamide are 0.13 uM and 0.06 uM respectively.

What is claimed is:

1. A compound of formula I:

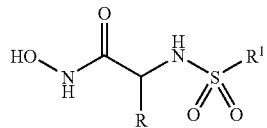

FORMULA I or a pharmaceutically acceptable salt thereof, wherein:
- $R^1$ is selected from the group consisting of $C_{6-10}$ aryl groups, said aryl groups optionally substituted with 1 to 3 groups of $R^a$;
- $R^a$ is selected from the group consisting of $C_{1-6}$ alkyl and halogen groups; and
- R is selected from the group consisting of $C_{3-10}$ heterocycloalkyl groups.

2. The compound according to claim 1, wherein $R^1$ is a phenyl group optionally substituted with 1 to 3 groups of $R^a$.

3. The compound according to claim 1, wherein $R^1$ is a phenyl group substituted with 1 to 3 groups of halogen, methyl, ethyl, propyl, butyl, or a mixture thereof.

4. The compound according to claim 1, wherein the compound is selected from the group consisting of:

N-hydroxy-2(R)-[(4-fluoro-3-methylphenylsulfonyl)]amino-2-(4'-tetrahydropyranyl)-acetamide;

compounds provided in Table 1 below

TABLE 1

| Example # | $R_1$ | $R_2$ |
|---|---|---|
| 64 | tetrahydropyranyl | 4-fluorophenyl |

TABLE 1-continued

| Example # | $R_1$ | $R_2$ |
|---|---|---|
| 74 | tetrahydropyranyl | 3,4-difluorophenyl |
| 78 | tetrahydropyranyl | 3,5-dichlorophenyl |
| 105 | piperidinyl | 3-methylphenyl |
| 130 | tetrahydropyranyl | 3-fluorophenyl | and a pharmaceutically acceptable salt thereof.

5. The compound according to claim 4, wherein the compound is
N-hydroxy-2(R)-[(4-fluoro-3-methylphenylsulfonyl)]amino-2-(4'-tetrahydropyranyl)-acetamide;
or a pharmaceutically acceptable salt thereof.

6. A composition comprising a compound according to claim 1 and a pharmaceutically acceptable carrier.

7. A composition comprising a compound according to claim 4 and a pharmaceutically acceptable carrier.

8. A composition comprising a compound according to claim 5 and a pharmaceutically acceptable carrier.

* * * * *